(12) United States Patent
Gray

(10) Patent No.: US 9,950,012 B2
(45) Date of Patent: *Apr. 24, 2018

(54) METHODS FOR REJUVENATING RED BLOOD CELLS

(71) Applicant: Biomet Biologics, LLC, Warsaw, IN (US)

(72) Inventor: Alan Gray, North Reading, MA (US)

(73) Assignee: Biomet Biologics, LLC, Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/748,565

(22) Filed: Jun. 24, 2015

(65) Prior Publication Data

US 2015/0290247 A1  Oct. 15, 2015

Related U.S. Application Data

(63) Continuation of application No. 13/756,116, filed on Jan. 31, 2013, now Pat. No. 9,102,918.

(51) Int. Cl.
| | |
|---|---|
| A01N 63/00 | (2006.01) |
| A61K 35/18 | (2015.01) |
| C12N 5/078 | (2010.01) |
| A61M 1/36 | (2006.01) |
| A61M 1/02 | (2006.01) |
| A61K 47/00 | (2006.01) |

(52) U.S. Cl.
CPC .............. *A61K 35/18* (2013.01); *A61K 47/00* (2013.01); *A61M 1/0209* (2013.01); *A61M 1/0218* (2014.02); *A61M 1/0272* (2013.01); *A61M 1/0281* (2013.01); *A61M 1/3621* (2013.01); *A61M 1/3692* (2014.02); *A61M 1/3693* (2013.01); *C12N 5/0641* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 3,874,384 A | 4/1975 | Deindoerfer et al. | |
| 4,004,586 A | 1/1977 | Christensen et al. | |
| 4,116,646 A | 9/1978 | Edwards | |
| 4,786,286 A | 11/1988 | Cerny et al. | |
| 4,994,039 A | 2/1991 | Mattson | |
| 5,098,371 A | 3/1992 | Juji et al. | |
| 5,250,303 A | 10/1993 | Meryman et al. | |
| 6,059,968 A | 5/2000 | Wolf, Jr. | |
| 6,190,855 B1 | 2/2001 | Herman et al. | |
| 7,723,017 B2 | 5/2010 | Bitensky et al. | |
| 9,102,918 B2 | 8/2015 | Gray | |
| 9,103,842 B2 | 8/2015 | Gray et al. | |
| 9,550,015 B2 | 1/2017 | Gray | |
| 2001/0036624 A1 | 11/2001 | Sumita et al. | |
| 2001/0052497 A1 | 12/2001 | Blickhan et al. | |
| 2002/0063090 A1 | 5/2002 | Calhoun et al. | |
| 2002/0068873 A1 | 6/2002 | Sawamoto et al. | |
| 2004/0015147 A1 | 1/2004 | Mathias et al. | |
| 2005/0074743 A1 | 4/2005 | Purmal et al. | |
| 2005/0233302 A1 | 10/2005 | Hess et al. | |
| 2006/0180526 A1 | 8/2006 | Sugawara et al. | |
| 2007/0043317 A1 | 2/2007 | Sugawara | |
| 2007/0095764 A1 | 5/2007 | Yang | |
| 2007/0179424 A1 | 8/2007 | Rubinstein et al. | |
| 2008/0047898 A1 | 2/2008 | Sommer et al. | |
| 2008/0223798 A1 | 9/2008 | Paretta et al. | |
| 2011/0139276 A1 | 6/2011 | Kashmiran et al. | |
| 2011/0256522 A1 | 10/2011 | Ericson et al. | |
| 2011/0290260 A1 | 12/2011 | Tomes et al. | |
| 2012/0010596 A1 | 1/2012 | Siems et al. | |
| 2012/0077182 A1 | 3/2012 | Bitensky et al. | |
| 2012/0135391 A1 | 5/2012 | Shaz et al. | |
| 2013/0004937 A1 | 1/2013 | Yoshida et al. | |
| 2014/0065117 A1 | 3/2014 | Gray | |
| 2014/0212397 A1 | 7/2014 | Gray et al. | |
| 2014/0212400 A1 | 7/2014 | Gray | |
| 2014/0221958 A1 | 8/2014 | Gray | |
| 2015/0182678 A1 | 7/2015 | Gray | |
| 2015/0366911 A1 | 12/2015 | Gray et al. | |

FOREIGN PATENT DOCUMENTS

| | | |
|---|---|---|
| EP | 0987034 A2 | 3/2000 |
| JP | 2016508501 A | 3/2016 |
| JP | 2016508782 A | 3/2016 |
| WO | 0113933 A2 | 3/2001 |
| WO | 2011103179 A1 | 8/2011 |

(Continued)

OTHER PUBLICATIONS

Bandarenko et al., Transfusion, 2007, vol. 47, p. 680-686.*
Blood Banking and Transfusion Medicine, Basic Principles & Practice, Second edition, Christopher D. Hillyer et al., 2007, pp. 186, 187, 194 and 195 Only.*
Chaudhari, C.N., Mjafi, 2009, vol. 65, No. 1, p. 55-58.*
Brecher, M.E. et al. Rejuvenation of erythrocytes preserved with AS-1 and AS-3. A.J. Clin. Path. 96(6):767-769. 1991.
Burger, Patrick et al. An improved red blood cell additive solution maintains 2, 3-diphosphoglycerate and adenosine triphosphate levels by an enhancing effect on phosphofructokinase activity during cold storage. Transfusion, vol. 50, No. 11, (Nov. 29, 2010), pp. 2386-2392.
Button, L. et al. "Rejuvenation of red blood cells drawn in ADSOL to extend autologous red cell storage" (Abstract S54) 26(6): 558, 1986. Transfusion.

(Continued)

*Primary Examiner* — Kade Ariani
(74) *Attorney, Agent, or Firm* — Schwegman Lundberg & Woessner, P.A.

(57) ABSTRACT

Methods and a system for transfusing blood to a mammalian subject. The method includes obtaining a volume of donated red blood cells (RBCs), adding an enhancement composition to the RBCs to form a treated blood composition, incubating the treated blood composition to form an incubated blood composition, and administering the incubated blood composition to a patient. The system includes a functionally-closed, sterile Y-type tube set.

19 Claims, 3 Drawing Sheets

(56) References Cited

FOREIGN PATENT DOCUMENTS

| WO | 2014039660 A1 | 3/2014 |
|---|---|---|
| WO | WO-2014120431 A1 | 8/2014 |
| WO | WO-2014120919 A1 | 8/2014 |

OTHER PUBLICATIONS

Caridian BCT. COBE Spectra, Apheresis System. "Customized White Blood Cell Collections" 2009.
D'Alessandro, Angelo et al. Red blood cell strage: the story so far. Blood Transfus, (Mar. 29, 2010), pp. 82-88.
Dufour SP, et al; Erythrocyte-Dependent Regulation of Human Skeletal Muscle Blood Flow: Role of Varied Oxyhemoglobin and exercise on nitrite, S-nitrosohemoglobin, and ATP. Am J Physiol Heart Circ Physiol 299:H1936-H1946, (2010).
Haemonetics, ACP 215 Automated Cell Processor (2012).
Heaton, A. et al. "Use of ADSOL preservation solution for prolonged storage of low viscosity AS-1 red blood cells." BR. J. Haemo. 57:467-468, 1984.
Hess, J.R. An update on solutions for red cell storage. Vox Sanguinis, vol. 91, No. 1 (Jul. 1, 2006) pp. 13-19.
Hess, John R., Red cell storage. Journal of Proteomics, Elsevier, Amsterdam, NL., vol. 73, No. 3, (Jan. 3, 2010), pp. 368-373.
Hospira. "GemStar Pump Set-SL, Nonvented with 0.2 Micron Filter, 96 Inch." (2012).
Klein et al., "Red Blood Cell Transfusion in Clinical Practice" The Lancet, (Aug. 4, 2007), vol. 370, pp. 415-426.
Liu et al., "Microfluidic Chip Toward Cellular ATP and ATP-Conjugated Metabolic Analysis with Bioluminescence Detection" Analytical Chemistry, (Jan. 15, 2005), vol. 77, No. 2, pp. 573-578.
Lockwood et al. "Effects of Rejuvenation and Frozen Storage on 42-Day-Old AS-3 RBCs" Transfusion, (Nov. 2003) vol. 43, pp. 1527-1532.
Meyer, E. K. et al. "Rejuvenation capacity of red blood cells in additive solutions over long-term storage." Transfusion. Jul. 2011, vol. 51, No. 7: 1574-1579.
Rathburn, E.J. "Posttransfusion survival of red cells frozen for 8 weeks after 42-day liquid storage in AS-3." Transfusion 29(3):213-217, 1989.
Rejuvenation Handbook, A Comprehensive Guide to Red Cell Rejuvenation, enCyte™ Systems Inc., Brochure, (1977).
ReJuvesol® Red Blood Cell Processing Solution, enCyte™ Systems, Inc., Brochure (Mar. 1997).
Resnick, LM et al., "Is the Higher Incidence of Ischemic Disease in Patients with Hypertension and Diabetes Related to Intracellular Depletion of High Energy Metabolites?" Am J Med Sci Feb. 1994; 307 Suppl 1:S66-9.
Reynolds JD, et al. "The Transfusion Problem: Role of Aberrant S-Nitrosylation" Transfusion, 51:852-858, 2011.
Roback JD, "Vascular Effects of the Red Blood Cells Storage Lesion" Transfusion Medicine, ASH Education Book. Dec. 10, 2011 vol. 2011 No. 1 475-479.
Scott, K. L. et al. "Biopreservation of Red Blood Cells: Past, Present, and Future" Transfusion Medicine Reviews, Grune and Stratton, Orlando, FL (2005) vol. 19 No. 2: 127-142.
Song et al. "Multiplexed volumetric bar-chart chip for point-of-care diagnostics" Nat Commun. (2012) 3:1283.
Spiess et al. Pro: Autologous blood should be available for elective cardiac surgery. Journal of Cardio Thoracic and Vascular Anesthesia, Saunders, Philadelphia, PA, US, vol. 8, No. 2 (Apr. 1, 1994), pp. 231-237.
Stan et al., Rom. J. Intern. Med., 2009, vol. 47, No. 2, p. 173-177.
Valeri, C.R. "Simplification of the method for adding and removing glycerol during freezing preservation of human red blood cells with the high or low glycerol methods: Biochemical Modification prior to freezing." Trasfusion 15 (3):195-218, 1975.
Valeri, C.R. et al. The survival, function and hemolysis of human RBCs stored at 4C in additive solution (AS-1, AS-3 or AS-5) for 42 days and then biochemically modified, frozen, thawed washed and stored at 4C in sodium chloride and glucose solution for 24 hours. Transfusion, American Association of Blood Banks, Bethesda, MD, US, vol. 40 (Nov. 1, 2000), pp. 1341-1345.
Valeri, C.R. et al. "A clinical experience with ADSOL preserved erythrocytes" Surg. Gyn. Obs. 166:33-46, 1988.
Valeri, C.R. et al., "Automation of the glycerolization of red blood cells with the high-separation bowl in the Haemonetics ACP 215 Instrument" Transfusion 2005, vol. 45, p. 1621-1627.
Valeri, C.R., Rejuvenation and Freezing of Outdated Stored Human Red Cells, New England Journal of Medicine 287:1.307-1313 (Dec. 28, 1972).
Van De Watering, L.M. G, et al. Beneficial Effects of Leukocyte Depletion of Transfused Blood on Postoperative Complications in Patients Undergoing Cardiac Surgery: A Randomized Clinical Trial. Circulation, vol. 97, No. 6, (Feb. 17, 1998), pp. 562-568.
Veale, Margaret F. et al. Effect of additive solutions on red blood cell (RBC) membrane properties of stored RBCs prepared from whole blood held for 24 hours at room temperature. Transfusion Jan. 2011, vol. 51, Suppl 1, (Jan. 2011), pp. 255-335.
Yoshida, T., et al. The effects of additive solution pH and metabolic rejuvenation on anaerobic storage of red cells, Transfusion, vol. 48, No. 10, (Oct. 1, 2008), pp. 2096-2105.
Zimrin, A.B. et al. Current issues relating to the transfusion of stored red blood cells. Vox Sanguines, vol. 96, No. 2, (Feb. 1, 2009), pp. 93-103.
NPL text search results, (Oct. 24, 2013), 2 pgs.
"U.S. Appl. No. 13/756,116, 312 Amendment filed May 26, 2015", 6 pgs.
"U.S. Appl. No. 13/756,116, Advisory Action dated Aug. 6, 2014", 3 pgs.
"U.S. Appl. No. 13/756,116, Examiner Interview Summary dated Jan. 26, 2015", 3 pgs.
"U.S. Appl. No. 13/756,116, Final Office Action dated May 5, 2014", 9 pgs.
"U.S. Appl. No. 13/756,116, Non Final Office Action dated Oct. 3, 2014", 12 pgs.
"U.S. Appl. No. 13/756,116, Non Final Office Action dated Oct. 29, 2013", 8 pgs.
"U.S. Appl. No. 13/756,116, Notice of Allowance dated Feb. 27, 2015", 7 pgs.
"U.S. Appl. No. 13/756,116, PTO Response to Rule 312 Communication dated Jul. 9, 2015", 2 pgs.
"U.S. Appl. No. 13/756,116, Response filed Feb. 3, 2015 to Non Final Office Action dated Oct. 3, 2014", 11 pgs.
"U.S. Appl. No. 13/756,116, Response filed Feb. 26, 2014 to Non Final Office Action dated Oct. 29, 2013", 18 pgs.
"U.S. Appl. No. 13/756,116, Response filed Jul. 29, 2014 to Final Office Action dated May 5, 2014", 13 pgs.
"U.S. Appl. No. 13/756,116, Response filed Sep. 5, 2014 to Advisory Action dated Aug. 6, 2014", 12 pgs.
"U.S. Appl. No. 13/844,773, 312 Amendment filed May 6, 2015", 6 pgs.
"U.S. Appl. No. 13/844,773, Advisory Action dated Aug. 5, 2014", 3 pgs.
"U.S. Appl. No. 13/844,773, Examiner Interview Summary dated Jan. 23, 2015", 3 pgs.
"U.S. Appl. No. 13/844,773, Final Office Action dated Jun. 2, 2014", 13 pgs.
"U.S. Appl. No. 13/844,773, Non Final Office Action dated Sep. 26, 2014", 14 pgs.
"U.S. Appl. No. 13/844,773, Non Final Office Action dated Dec. 26, 2013", 11 pgs.
"U.S. Appl. No. 13/844,773, Notice of Allowance Feb. 13, 2015", 8 pgs.
"U.S. Appl. No. 13/844,773, PTO Response to Rule 312 Communication dated May 13, 2015", 2 pgs.
"U.S. Appl. No. 13/844,773, Response filed Jan. 26, 2015 to Non Final Office Action dated Sep. 26, 2014", 12 pgs.
"U.S. Appl. No. 13/844,773, Response filed Mar. 26, 2014 to Non Final Office Action dated Dec. 26, 2013", 19 pgs.
"U.S. Appl. No. 13/844,773, Response filed Jul. 29, 2014 to Final Office Action dated Jun. 2, 2014", 13 pgs.
"U.S. Appl. No. 13/844,773, Response filed Nov. 21, 2013 to Restriction Requirement dated Nov. 6, 2013", 2 pgs.

(56) References Cited

OTHER PUBLICATIONS

"U.S. Appl. No. 13/844,773, Restriction Requirement dated Nov. 6, 2013", 5 pgs.
"U.S. Appl. No. 14/748,649, Non Final Office Action dated May 19, 2016", 16 pgs.
"U.S. Appl. No. 14/748,649, Response filed Aug. 17, 2016 to Non Final Office Action dated May 19, 2016", 10 pgs.
"COBE 2991 Cell Processor", CaridianBCT, (2008), 4 pgs.
"European Application Serial No. 14707864.6, Response filed Apr. 25, 2016 to Communication pursuant to Rules 161(1) and 162 EPC dated Oct. 14, 2015", 20 pgs.
"International Application Serial No. PCT/US2014/013845, International Preliminary Report on Patentability dated Aug. 13, 2015", 9 pgs.
"International Application Serial No. PCT/US2014/013845, International Search Report dated May 13, 2014", 5 pgs.
"International Application Serial No. PCT/US2014/013845, Written Opinion dated May 13, 2014", 7 pgs.
U.S. Appl. No. 13/756,712, filed Feb. 1, 2013, Functionally-Closed, Sterile Blood Precessing Solution System and Method, U.S. Pat. No. 9,011,408.
U.S. Appl. No. 14/634,264, filed Feb. 27, 2015, Functionally-Closed, Sterile Blood Processing System and Method, U.S. Pat. No. 9,550,015.
"U.S. Appl. No. 13/756,712, 312 Amendment filed Feb. 19, 2015", 3 pgs.
"U.S. Appl. No. 13/756,712, Non Final Office Action dated Oct. 9, 2014", 22 pgs.
"U.S. Appl. No. 13/756,712, Notice of Allowance dated Feb. 4, 2015", 13 pgs.
"U.S. Appl. No. 13/756,712, PTO Response to Rule 312 Communication dated Mar. 18, 2015", 2 pgs.
"U.S. Appl. No. 13/756,712, Response filed Jan. 9, 2015 to Non Final Office Action dated Oct. 9, 2014", 18 pgs.
"U.S. Appl. No. 13/756,712, Response filed Sep. 16, 2014 to Restriction Requirement dated Jul. 17, 2014", 5 pgs.
"U.S. Appl. No. 13/756,712, Restriction Requirement dated Jul. 17, 2014", 7 pgs.
"U.S. Appl. No. 14/634,264, Non Final Office Action dated Jul. 15, 2016", 11 pgs.
"U.S. Appl. No. 14/634,264, Notice of Allowance dated Oct. 31, 2016", 9 pgs.
"U.S. Appl. No. 14/634,264, Preliminary Amendment dated Feb. 27, 2015", 7 pgs.
"U.S. Appl. No. 14/634,264, Response filed Oct. 17, 2016 to Non Final Office Action dated Jul. 15, 2016", 8 pgs.
"U.S. Appl. No. 14/748,649, Final Office Action dated Mar. 22, 2017", 9 pgs.
"European Application Serial No. 14702699.1, Response filed Mar. 14, 2016 to Communication pursuant to Rules 161(2) and 162 EPC dated Sep. 8, 2015", 17 pgs.
"European Application Serial No. 14707864.6, Communication Pursuant to Article 94(3) EPC dated Nov. 24, 2016", 17 pgs.
"European Application Serial No. 14707864.6, Communication Pursuant to Article 94(3) EPC dated Nov. 24, 2016", 4 pgs.
"International Application Serial No. PCT/US2014/011451, International Preliminary Report on Patentability dated Aug. 13, 2015", 9 pgs.
"International Application Serial No. PCT/US2014/011451, International Search Report dated Jun. 3, 2014", 3 pgs.
"International Application Serial No. PCT/US2014/011451, Written Opinion dated Jun. 3, 2014", (7 pgs).
Klein, et al., "Red Blood Cell Transfusion in Clinical Practice", The Lancet, vol. 370 (Aug. 4, 2007), 415-426.
Resnick, et al., "Is the Higher Incidence of Ischemic Disease in Patients with Hypertension and Diabetes Related to Intracellular Depletion of High Energy Metabolites?", A. J. Medical Sciences 307, Suppl. 1,, (1994), 1 pg.
"U.S. Appl. No. 14/748,649, Notice of Allowance dated Jul. 11, 2017", 10 pgs.
"U.S. Appl. No. 14/748,649, PTO Response to Rule 312 Communication dated Oct. 5, 2017", 2 pgs.
"U.S. Appl. No. 14/748,649, Response filed Jun. 22, 2017 to Final Office Action dated Mar. 22, 2017", 12 pgs.
Creamer, K., et al., "Pediatric Surgery and Medicine for Hostile Environments", (Second Ed. 2016), Chapter 5 http://www.cs.amedd.army.mil/FileDownloadpublic.aspx?docid=542434d9-796c-410e-9ce7-75acc38134c4, (2016), 37-42.
Morris, K. P., et al., "A new formula for blood transfusion volume in the critically ill", Arch Dis Child; vol. 90, (2005), 724-728.

\* cited by examiner

METHODS FOR REJUVENATING RED BLOOD CELLS

RELATED APPLICATIONS

This application is a continuation application of U.S. patent application Ser. No. 13/756,116, filed on Jan. 31, 2013, issued as U.S. Pat. No. 9,102,918 on Aug. 11, 2015, which patent disclosure is incorporated herein by reference in its entirety.

INTRODUCTION

The present disclosure relates to methods for transfusing blood to mammalian subjects, and a system for use with the methods.

Transfusion of blood is an important aspect of treating many disorders and injuries, such as treatment of accident victims and during surgical procedures. According to current American Red Cross statistics, about 5 million people receive blood transfusions yearly in the United States alone. A single accident victim can require as many as 100 pints of blood. Thus, the collection and distribution of blood and blood products is a vital part of the health care system. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. Short term storage can be as long as six weeks, although blood or blood components can be frozen and stored for as long as ten years. Unfortunately, the storage of red blood cells (RBCs) is associated with "storage lesions," altering their energy production, oxygen delivery capacity, redox status, and structural/membrane integrity. For example, the concentration of adenine triphosphate (ATP) in stored RBCs decreases over time. Not only is ATP an energy source used by cells to catalyze numerous enzymatic reactions, ATP also signals endothelial cells to release nitric oxide (NO), which is a potent vasodilator. Additionally, the concentration of 2,3-diphosphoglycerate (2,3-DPG) within RBCs is significantly reduced after 14 days of storage, and is often undetectable after 21 days of storage. 2,3-DPG enhances the ability of RBCs to release oxygen by interacting with deoxygenated hemoglobin, decreasing the hemoglobin's affinity for oxygen, and thereby promoting the release of the remaining oxygen bound to the hemoglobin. Therefore, with diminished levels of ATP and 2,3-DPG, an RBC' s ability to oxygenate tissue is severely impaired.

To rejuvenate RBCs before administration into a patient, blood can be incubated with an enhancement composition containing materials that increase intracellular concentrations of 2,3-DPG and ATP, improving the ability of RBCs to oxygenate tissues. Such enhancement compositions typically comprise one or more active materials such as inosine, adenine, sodium pyruvate and sodium phosphate (dibasic and monobasic). A useful enhancement composition is rejuvesol® Red Blood Cell Processing Solution (rejuvesol® Solution), which has been marketed by Cytosol Laboratories Inc. (now Citra Labs, LLC) since 1991.

While such compositions are effective to improve the metabolic activity of RBCs, there remains a need to develop compositions and methods that improve efficacy. Moreover, it has been discovered that such compositions may have particular utility during medical procedures treating certain disorders.

SUMMARY

The present technology provides methods for transfusing blood to a mammalian subject, including such methods for the treatment of disorders associated with characterized by reduced tissue oxygenation. The methods comprise adding a red blood cell metabolic enhancement composition (herein "enhancement composition") to a volume of red blood cells, incubating the treated blood composition, and administering the incubated blood composition to the mammalian subject. In some embodiments, the incubated blood composition is washed prior to administration to the subject.

Aspects of the methods, such as the washing and the steps of adding the enhancement composition to the red blood cells, may be performed at the point of care for the mammalian subject. Such processes may be continuous, using a system proximate to the subject at the point of care, in fluid communication Methods can be performed immediately after blood is collected from a donor and prior to preservation, or the method can be performed after blood is removed from preservation, immediately before administration to a subject. Before the method is performed, the blood can be processed to become red blood cell concentrated (RBCC), or leukocytes can be removed to generate leukoreduced RBCs.

The present technology also provides a method for transfusing RBCs to a subject, at a point of care, comprising obtaining a volume of donated RBCs, adding an enhancement composition to the volume of donated RBCs to form a treated blood composition, incubating the treated blood composition to form an incubated RBC composition, diluting the incubated RBC composition with wash solution to form a diluted RBC composition, centrifuging the diluted RBC composition, forming a pellet of RBC and a supernatant, and administering the incubated blood composition to a subject. After washing, the washed RBC composition can be centrifuged to form a pellet of RBCs and a supernatant. The supernatant can be removed and the pellet can be resuspended in an additive solution, to form a resuspended RBC composition.

DRAWINGS

Figure 1:
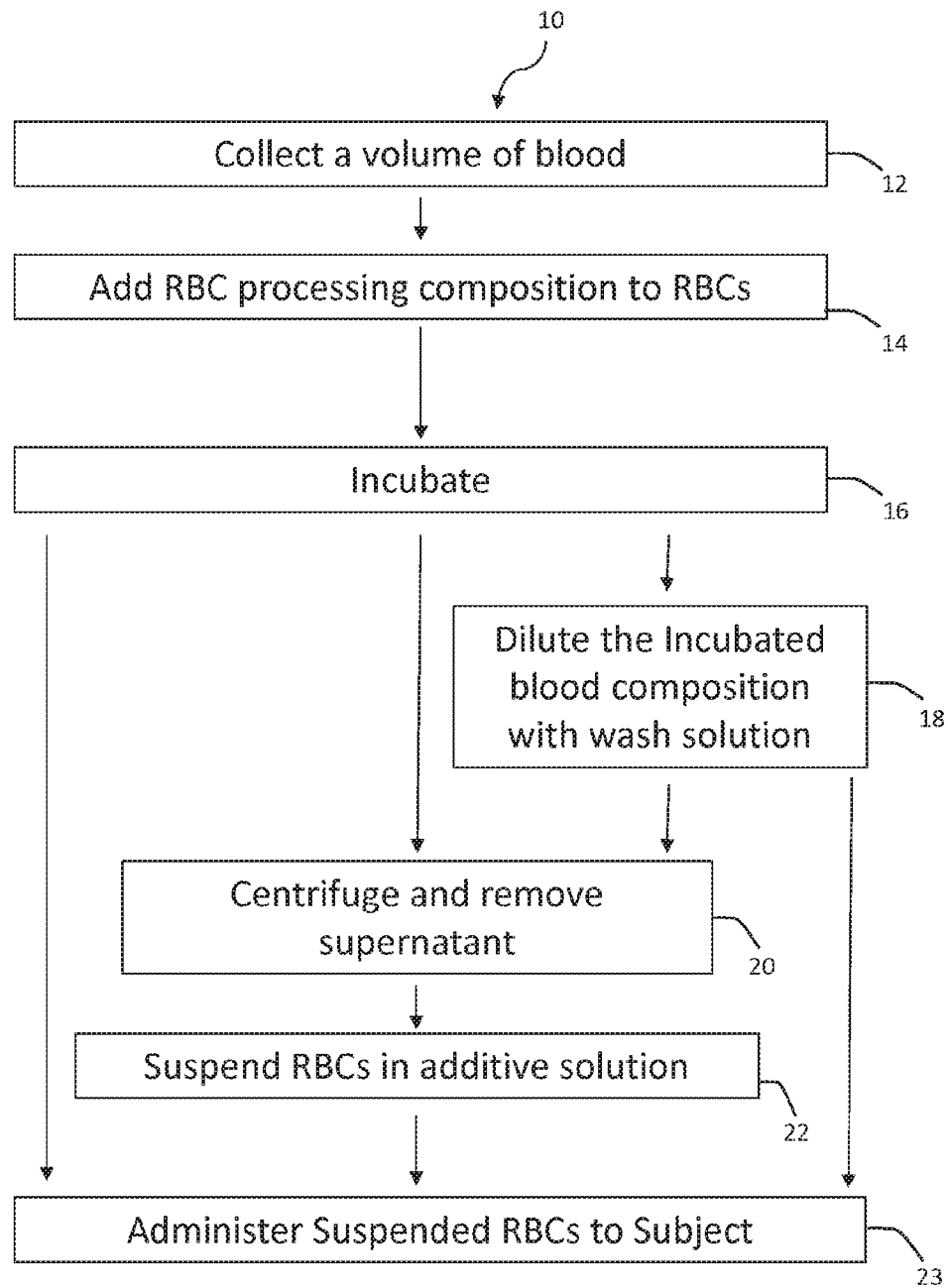
FIG. 1 is a diagrammatic illustration of a representative method for transfusing blood.

It should be noted that the figures set forth herein are intended to exemplify the general characteristics of an apparatus, materials and methods among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this The present technology relates to methods of processing whole blood or a blood fraction comprising red blood cells (herein, unless specifically stated otherwise, referred to as "blood") using a composition (referred to herein as an "enhancement composition"). Such compositions may comprise a rejuvenating material selected from the group consisting of inosine, adenine, pyruvate, phosphates, and mixtures thereof.

RBC Metabolic Enhancement Compositions

The present technology provides enhancement compositions which restore, increase or otherwise enhance, directly or indirectly, one or more metabolic functions of red blood cells. As further discussed below, in some embodiments, enhancement compositions increase the production or concentration of one or more intracellular constituents associated with the biochemical or biomechanical function of red blood cells, including oxygen transport, oxygen release or other metabolic parameters which affect the ability of blood to oxygenate tissue. As discussed further below, in some embodiments enhancement compositions increase the intracellular concentrations of adenine triphosphate (ATP) and 2,3-diphosphoglycerate (2,3-DPG).

In some embodiments, enhancement compositions of the present technology can comprise safe and effective amounts of inosine, pyruvate, adenine and phosphate. A "safe and effective" amount of a rejuvenating material is an amount that is sufficient to have the desired effect on the biochemical or biomechanical function of RBCs, without undue adverse side effects on the viability of RBCs or other blood components or a subject to whom the RBCs are administered (such as toxicity, irritation, or allergic response), commensurate with a reasonable benefit/risk ratio when used in the manner of this technology. The specific safe and effective amount of the rejuvenating material will, obviously, vary with such factors as the metabolic state of the RBCs, the specific rejuvenating material(s) used, the conditions under which the RBCs are processed with the rejuvenating material, and physical condition of the subject to whom the RBCs are administered.

In various embodiments, the inosine can have a concentration of from about 25 g/L to about 30 g/L. Preferably, the concentration of inosine can be about 25.0 g/L, about 25.5 g/L, about 26.0 g/L, about 26.2 g/L, about 26.4 g/L, about 26.6 g/L, about 26.8 g/L, about 27.0 g/L, about 27.5 g/L, about 28.0 g/L, about 28.5 g/L, about 29.0 g/L, about 29.5 g/L, or about 30.0 g/L. In various embodiments, the pyruvate can have a concentration of from about 5 g/L to about 15 g/L. Preferably, the concentration of pyruvate can be about 5 g/L, about 6 g/L, about 7 g/L, about 8 g/L, about 9 g/L, about 10 g/L, about 11 g/L, about 12 g/L, about 13 g/L, about 14 g/L, or about 15 g/L. In various embodiments, the adenine can have a concentration of from about 0.2 g/L to about 2 g/L. Preferably, the concentration of adenine can be about 0.2 g/L, about 0.3 g/L, about 0.4 g/L, about 0.5 g/L, about 0.6 g/L, about 0.7 g/L, about 0.8 g/L, about 0.9 g/L, about 1.0 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, or about 2.0 g/L. The phosphate can be a mixture of a monobasic monohydrate salt and a dibasic heptahydrate salt. The phosphate can be a salt of sodium phosphate. The ratio of monobasic salt to dibasic salt can be from about 1:2 to about 1:3. More specifically, the monobasic salt:dibasic salt ratio can be about 1:20, about 1:2.10, about 1:2.15, about 1:2.20, about 1:2.25, about 1:2.30, about 1:2.35, about 1:2.40, about 1:2.45, about 1:2.50, about 1:2.55, about 1:2.60, about 1:2.65, about 1:2.70, about 1:2.75, about 1:2.80, about 1:2.85, about 1:2.90, about 1.295, or about 1:30. The phosphate mixture can have a final concentration of from about 18 g/L to about 22 g/L. More specifically, the concentration of phosphate mixture can be about 18 g/L, about 18.5 g/L, about 19 g/L, about 19.5 g/L, about 20 g/L, about 20.1 g/L, about 20.2 g/L, about 20.3 g/L, about 20.4 g/L, about 20.5 g/L, about 20.6 g/L, about 20.7 g/L, about 20.8 g/L, about 20.9 g/L, about 21 g/L, about 21.5 g/L, or about 22 g/L.

In some embodiments, enhancement compositions comprise:

(a) about 27 (e.g, 26.8) g/L inosine;
(b) about 11 g/L pyruvate (e.g., sodium pyruvate);
(c) about 0.7 (e.g., 0.681) g/L adenine; and
(d) about 21 (e.g., 20.8) 1 g/L phosphate (e.g., a mixture of about 6.21 g/L monobasic, monohydrate; and about 14.6 g/L dibasic, heptahydrate).

Preferably, the composition has a pH of from about 6.5 to about 7.5, more preferably from about 6.6 to about 7.4, more preferably from about 6.7 to about 7.1, more preferably from about 6.7 to about 7.0. An enhancement composition useful in the methods of this technology has been commercialized by Citra Labs, LLC (formerly Cytosol Laboratories), Braintree, Mass., under the mark rejuvesol®.

Methods of Processing Blood

The present technology also provides to methods of processing whole blood or a blood fraction comprising red blood cells (herein, unless specifically stated otherwise, referred to as "blood") using an enhancement composition of this technology, as described above. Such methods comprise, for example:

1) mixing blood with an enhancement composition; and
2) incubating the mixture of blood and enhancement composition.

The blood treated in the present methods may be obtained from a mammalian subject (a "donor") using methods among those well known in the art. In various embodiments the donor is a human subject. The blood may be allogeneic (i.e., donated by a subject of the same species) or autologous (obtained by the subject to whom the treated blood is to be administered, such as may be drawn in advance of a surgical procedure).

Processing of blood using an enhancement composition of the present technology may be performed on blood that has been stored or may be performed on "fresh" blood at a time proximate to the time it is withdrawn from the donor. (As used herein, a "proximate" time is any time 24 hours or less after an initial event (e.g., donation of blood), such as concurrent with the event, or 18 hours, 12 hours, 6 hours, 4 hours, 2 hours, 1 hour, 30 minutes, 15 minutes, 10 minutes, 2 minutes, 1 minute, or less, after the initial event.) The volume of blood can be concentrated, by removal of at least a portion of blood plasma, to produce red blood cell concentrate (RBCC). Storage may be, for example, from 1 to 50 days, or longer, as needed. Storage may be at any temperature and other conditions to as to maintain viability of the RBCs for clinically acceptable storage period. For example, storage may be at a temperature of from about 1° C. to about 6° C. In other embodiments, the RBCs may be frozen, at a temperature of −65° C. or lower, with the addition of conditioning agents that preserve the viability of the RBCs at such low temperatures. Suitable conditioning agents (cryopreservatives) include glycerol. It is understood that such conditioning agents are to be removed from the RBCs prior to administration, such as by methods described below for removal of cryopreservatives prior to administration.

In some embodiments, the volume of blood is leukoreduced prior to use in the processes of the present technology. Such leukoreduced blood contains fewer leukocytes than whole blood, and may, in some embodiments, be essentially free of leukocytes. Other blood components may also be removed from leukoreduced blood, either before, during, or after removal of the leukocytes.

Incubating the mixture is conducted for a time sufficient to allow RBCs in the blood to assimilate components from the enhancement composition and achieve a desired effect on a biochemical or biomechanical function of RBCs. Without limiting the scope of methods, composition and uses of the present technology, the incubation may increase the metabolic activity of RBCs (for example, in the glycolysis, pentose phosphate, and amino acid pathways), restoring a metabolic profile in the RBC close to those in fresh RBC. This restored profile may result in improved RBC function in the transfusion recipient including oxygenation of tissues, nitric oxide (NO) production capacity, and reduced risk of adverse effect from the transfusion. For example, incubation may be conducted for a time sufficient to increase the concentration of ATP and 2,3-DPG in RBCs. The time may vary, depending on such factors as the desired level of increase of ATP and 2,3-DPG, the use of mechanical agitation, the amount of enhancement composition used, and temperature of the blood during incubation. In some embodiments, about 50 ml of enhancement composition is added to RBCs derived from up to about 550 ml of whole blood. Mixing can be performed by swirling, shaking, rotating, or agitating.

In some embodiments, the blood is tested during incubation to determine whether one or more desired biochemical or biomechanical attributes of the RBCs have been attained. Thus, for example, incubation may be conducted until a desired level of ATP, 2,3-DPG, NO or other biochemical marker of RBC function is attained, e.g., essentially equal to levels found in fresh blood.

Methods for measuring such markers of RBC function useful herein include methods among those known in the art. For example, 2,3-DPG can be detected by assay kits that are commercially available. In one such assay, 2,3-DPG from blood is split by phosphoglycerate mutase (PGM), when PGM is activated by glycolate-2-phosphate, to produce phosphoglycerate (PG) and inorganic phosphate ($P_i$). Both 2-PG and 3-PG can be formed, but 2-PG is isomerized by PGM to form 3-PG. In the presence of ATP, 3-PG is converted to 1,3-DPG by phosphoglycerate kinase (PGK). Next, 1,3-DPG is converted to glyceraldehyde-3-P by glyceraldehyde-3-phosphate dehydrogenase (GAP-DH) and the oxidation of NADH. Glyceraldehyde-3-P is converted to digydroxyacetone-P by triosephosphate isomerase (TIM), and dihydroxyacetone-P is converted to glycerol-3-P by glycerol-3-phosphate dehydrogenase (GDH) and the oxidation of NADH. The oxidation of the two NADH molecules can be monitored spectrophotometrically at a wavelength of 340 nm. Where necessary, standard curves can be prepared with standard solutions of 2,3-DPG. A kit useful in such methods is commercially available from Roche Diagnostics Corporation—Roche Applied Science (Indianapolis, Ind.), for the determination of 2,3-DPG in blood in the range of 0.02-0.15 µmol. In some embodiments, a sample of blood can be taken directly from a subject, or from a closed system used in a continuous process (as described below), for the 2,3-DPG determination. The difference between the 2,3-DPG before and after blood has been rejuvenated can be determined.

In another method, as an alternative to measuring 2,3-DPG, the partial pressure of $O_2$ gas required to achieve 50% hemoglobin saturation ($P_{50}$) is measured. For example, the $P_{50}$ can be measured at a point of care by use of a GEM Premier 3000 (Instrumentation Laboratory Company, Bedford, Mass.). In particular, a blood sample is mixed with heparin to prevent coagulation. Then, a drop or two of the blood sample is expelled onto a gauze pad. The gauze pad is then positioned at the GEM Premier 3000 for the $P_{50}$ analysis. This analysis can be performed before and after the blood has been rejuvenated.

ATP can be detected in blood by a bioluminescence assay. One such assay utilizes luciferase (typically recombinant firefly luciferase), which in the presence of ATP, converts luciferin to oxyluciferin. The oxyluciferin is produced in an electronically excited state. Therefore, the oxyluciferin releases a photon of light as it returns to its ground state. To measure the ATP present in blood, a blood sample can be drawn from a patient or from tubing containing treated or untreated blood. A small sample of the blood can be mixed with a luciferin/luciferase solution. The solution can be a buffer, such as a Tricine buffer, pH 7-8, containing luciferin, luciferase, and $Mg^{2+}$. The ATP in the blood sample will activate the reaction, which results in luminescence. The luminescence can be detected in a luminometer. Measurements can be taken before and after blood has been rejuvenated. Although the reagents for this ATP assay are individually available through multiple vendors, some vendors offer kits that comprise all the reagents. One such kit is the ATP Determination Kit (A22066) from Molecular Probes, Inc. (Eugene, Oreg.; now Life Technologies, Carlsbad, Calif.).

The blood may be incubated with an enhancement composition for a predetermined time, such as from about 30 seconds to about 24 hours. If the blood is to be stored prior to administration, incubation may occur throughout the period in which blood is stored, as discussed further below. For example, the blood can be incubated with an enhancement composition for from about 5 minutes to about 90 minutes, or from 15 minutes to about 60 minutes, at a temperature of from about 1° C. to about 45° C., or from about 25° C. to about 40° C., such as at about 37° C. In some embodiments, the blood is incubated for about 30 minutes.

Incubation can be performed using a variety of devices and methods among those known in the art. For example, blood can be incubated by immersing a bag containing the mixture of blood and enhancement composition in a recirculating water bath. In another embodiment, incubating can be performed for about 5 minutes to about 60 minutes (such as for about 30 minutes) in a thawing device with a bath temperature set at from about 25° C. to about 45° C. Thawing devices include ThermoLine Models: MT202, MT204, or MT210 sold by Helmer Scientific, Noblevilles, Ind., USA, (formerly ThermoGenesis, Corp, Rancho Cordova, Calif., USA). In another example, incubating can be performed by placing the treated blood composition in an insulated box containing about 6 instant hot gel packs, wherein the temperature within the insulated box is from about 25° C. to about 45° C. A device can be placed within the insulated box to mix the treated blood composition, or the insulated box can be rotated in such a way that the treated blood composition is mixed from within.

The treated fresh blood may be stored after incubation, or may be administered to a mammalian subject in need of blood. Conditions for storage include those discussed above. In some embodiments, the administration is at a time proximate to the time when the blood is obtained and treated using methods of the present technology.

In some embodiments, the processed RBC compositions of the present technology are sterilized. Sterilization can be performed by any pharmaceutically acceptable method, including such methods as are known to those of ordinary skill in the art. Non-limiting examples of sterilization include heating, autoclaving, irradiation, and filtering.

Methods may further comprise washing the blood after incubation to remove all, or a portion, of the components of the enhancement composition. Washing can be performed using methods among those known in the art, including such methods as are used for processing frozen blood to remove glycerol prior to transfusion. For example, washing may comprise adding a wash solution to a liquid volume of RBCs, centrifuging the resulting mixture to form a pellet of RBCs, and removing the supernatant. Wash solutions may include, for example, normal saline. Such washing may be performed with devices known in the art, such as the ACP® 215 Automated Cell Processor, sold by Haemonetics Corporation, Braintree, Mass. The washing may be performed at a time proximate to administration of the blood to a mammalian subject.

In some embodiments, methods comprise removing liquid components of the incubated red blood cell composition prior to administration to a mammalian subject. Such methods further comprise, for example, centrifuging the incubated red blood cell composition, forming a pellet of red blood cells, and a supernatant; and isolating the pellet of red blood cells. The pellet of red blood cells may then be suspended in an additive solution, forming a red blood cell suspension that may be administered to a mammalian subject. Additive solutions include those known in the art suitable for storage or administration of blood, including normal saline. In some embodiments, such methods further comprising adding a wash solution, such as normal saline, to the incubated red blood cell composition prior to the centrifuging. Thus, methods of the present technology include those comprising:
 (a) obtaining a volume of red blood cells from a mammalian subject;
 (b) adding an enhancement composition to the volume of red blood cells, forming a treated blood composition;
 (c) incubating the treated blood composition, forming an incubated red blood cell composition;
 (d) centrifuging the incubated red blood cell composition, forming a pellet of red blood cells, and a supernatant;
 (e) isolating the pellet of red blood cells; and
 (f) suspending the pellet of red blood cells in additive solution, forming a red blood cell suspension.

Optionally, the process may further comprise diluting the incubated red blood cell composition with wash solution prior to the centrifuging step.

Methods of the present technology may be continuous, wherein two or more sequential steps (e.g., adding an enhancement solution and incubating) are performed on a flow of RBCs, substantially without interruption through the process steps. Thus, for example, a liquid volume of RBCs may flow through an apparatus which adds enhancement solution, subjects the mixture of RBCs and enhancement solution to isolation conditions (e.g., heating and mixing). Such a flow may then continue in a continuous manner to further process steps, including addition of a washing solution, centrifugation, and suspension of RBCs. As discussed below, such processes may be performed in an automated closed system in fluid communication with an intravenous catheter.

Methods of Transfusing and Treatment

The present technology relates to methods for transfusing blood to a subject. Such methods comprise any procedure suitable for administering to a mammalian subject a liquid volume of blood comprising RBCs that have been processed according to a method of this technology. As further discussed below, transfusing may be performed pursuant to any medically appropriate procedure, such as for the treatment of diseases or disorders associated with blood loss or reduced blood function. Specific methods for administration include those known in the art, such as through use of an intravenous catheter.

The present technology provides methods where the processing of blood is performed at a time proximate to the administration of the processed blood. For example, as defined above, such proximate administration of blood may be performed 1 hour, 30 minutes, 15 minutes, 10 minutes, 2 minutes, 1 minute, or less, after incubation of the red blood cells. In some processes, the methods are "point of care," wherein the processes of the present technology are performed at a location proximate, such as in the same room (for example, bed side) or otherwise immediately adjacent, to the mammalian subject to be transfused with the RBCs. As further discussed below, such point-of-care processes may be performed using a system comprising an apparatus adapted to perform two or more sequential steps of a process of the present invention, such as the steps of obtaining blood, adding an enhancement composition, incubating, washing, and administering. In some embodiments, such a system is in fluid communication with a device, such as an intravenous catheter, for obtaining blood from a subject or administering blood to a subject. In some embodiments, the RBCs administered are autologous.

As discussed above, a subject in need of a transfusion can have a disorder characterized by reduced tissue oxygenation. Such disorders include those wherein when blood flow is fixed, restricted, reduced, or stopped. Furthermore, blood transfusions can be necessary when blood is lost though injury, surgery or disease. Subjects and disorders that may be treated include: subjects with sepsis or septic shock that are anemic and require a blood transfusion; subjects with Upper Gastrointestinal Bleeding ("UGIB") that are anemic and require a blood transfusion; subjects subjected to severe trauma that are anemic and require a blood transfusion; subjects that are critically ill (adult and pediatric) in an intensive care unit, who are anemic and require a blood transfusion; subjects that under-go open heart surgery and receive a blood cardioplegia solution to perfuse the heart during hypothermic, ischemic cross-clamp, thus providing better oxygenation of the myocardium during open-heart surgery; subjects suffering a stroke, treating ischemic brain tissue following a stroke, thus increasing the oxygen delivery capacity of the systemic circulation via exchange transfusion or by direct administration to the ischemic area via arterial catheter or by retrograde perfusion via the venous circulation; subjects undergoing obstetrical complications, subjects with bleeding ulcers; subjects with hemolytic anemia; and subjects with thrombocytopenia.

Further to the discussion above of methods involving centrifugation of incubated RBC volume, FIG. 1 shows an exemplary method 10 for transfusing blood to a mammalian subject. In step 12, a volume of blood is collected from a donor. The volume of blood can be obtained from the subject to whom the blood will be transfused, i.e. autologous blood, or the volume of blood can be allogeneic from a suitable donor. In some embodiments, the volume of blood is stored in various additive solutions, commonly used in the art, at 1° C.-6° C. In some embodiments, the volume of blood is cryopreserved. The volume of blood can be processed by concentrating to produce red blood cell concentrate (RBCC), or by removing leukocytes to produce leukoreduced RBCs (LR-RBCs; whereas non-leukoreduced blood is NLR-RBC). In yet other embodiments, the volume of blood is treated with a red blood cell (RBC) enhancement composition before being stored. Alternatively, the method 10 can be performed at a time proximate to when the volume of blood is collected.

In step 14, an enhancement composition is added to the volume of RBCs, forming a treated blood composition. The enhancement composition can be transferred through a functionally-closed sterile fluid pathway, such as described below. Next, in step 16, the treated blood composition is incubated, forming an incubated blood composition.

In optional step 18, the incubated blood composition can be diluted with saline or other wash solution, to form a diluted blood composition. The incubated blood composition can be transfused within 24 hours of washing or washing.

In step 20, the incubated blood composition from step 16, or the diluted blood composition from step 18, is centrifuged. Centrifuging results in a pellet of RBCs and a supernatant. The supernatant can be removed. In optional step 22, the pellet of RBCs is suspended in an additive solution, such as saline.

Finally, in step 23, any of the incubated blood composition from step 16, the diluted blood composition form step 18, or the resuspended blood composition from step 22 can be transfused to a subject.

Systems

As discussed above, processes of the present technology may be performed in a system apparatus adapted to perform two or more sequential steps of a process of the present invention in a continuous process. For example, one such system comprises:

(a) an incubation system, for mixing an enhancement composition with a volume of RBCs, which may be in fluid communication with a supply volume of the enhancement solution, and which may comprise a temperature control device for maintaining the temperature of the volume of RBCs during incubation;
(b) a washing system, for adding a washing solution to incubated RBCs;
(c) a centrifugation system, for isolating RBCs from the liquid volume of incubated RBCs; and
(d) a suspension system for adding a volume of additive solution to the isolated RBCs, to form an RBC suspension.

In some point of care embodiments, the system is in fluid communication with an intravenous catheter or other device by which the RBC suspension is directly administered to a subject. In the alternative, or in addition, the system may be in communication with a second intravenous catheter for obtaining a volume of whole blood directly from a subject, which may be the same subject to which the RBC suspension is administered.

In some embodiments, the system is automated, such that one or more steps of a process of this technology are performed without substantial intervention by a clinical operator during the process steps. Preferably, such systems are "closed," to minimize or eliminate exposure of the RBCs, the enhancement composition and other compositions used in the process to microbial contamination.

As discussed above, incubation of the blood may be conducted until a desired level of a biochemical marker of RBC function is attained. Thus, the incubation system may comprise a measurement device by which an aliquot of blood may be obtained and tested for the concentration of the marker, and the duration of incubation adjusted accordingly. For example, 2,3-DPG can be detected online by injecting reagents for a 2,3-DPG assay, such as is available from Roche Diagnostics Corporation—Roche Applied Science (Indianapolis, Ind.), as described above, into a tube of the closed system. The tube can comprise a transparent section, such as made from quartz, which can be positioned in a spectrophotometer. The difference between the 2,3-DPG before and after blood has been rejuvenated can be determined. In another embodiment, ATP can be detected online in a closed system, by injecting a luciferin/luciferase solution (as described above) into a transparent section of tubing in the system that contains blood. This transparent section of tubing can be enclosed in a dark box wherein no external light can enter. A photomultiplier tube (PMT) connected to an external computer is positioned immediately below the transparent tubing within the dark box. The PMT can detect light produced by the assay, and a computer can display the results. Measurements can be taken before and after blood has been rejuvenated.

Figure 2:
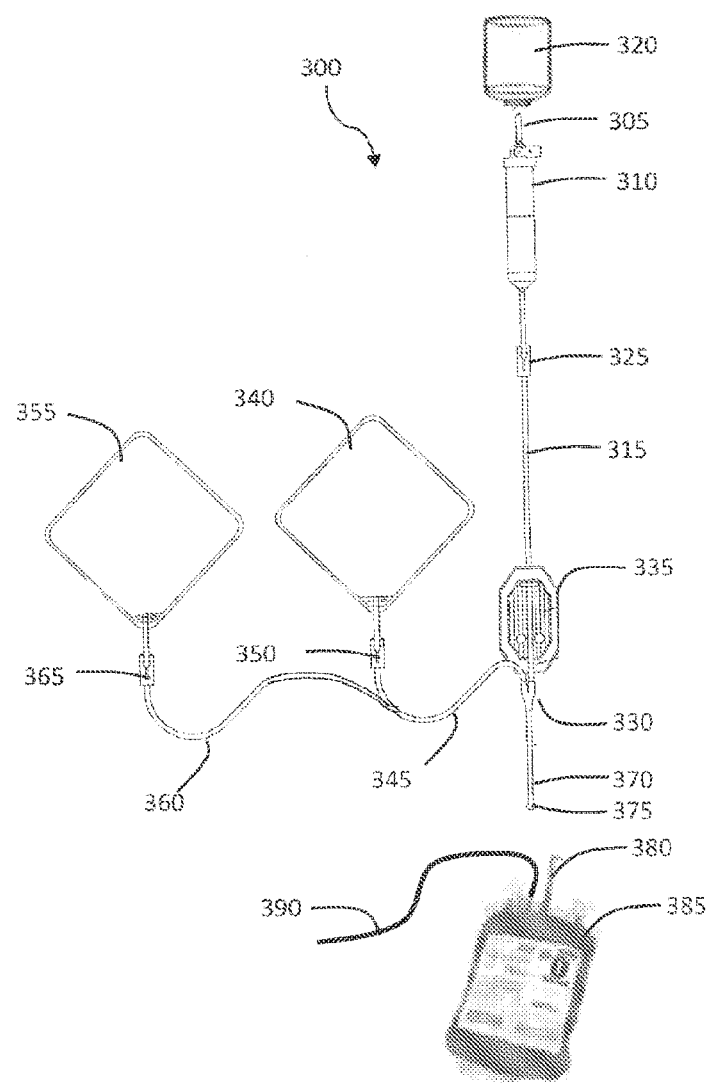
FIG. 2 is a diagrammatic illustration of an apparatus for improving the metabolic function of blood.

FIG. 2 depicts a closed, Y-type tube set 30 system useful in methods of the present technology. The tube set 30 includes a vented spike 32 with drip chamber 34 coupled to the distal end of a first tube 36. Spike 32 can be inserted into a blood treatment vial 38 or bottle to complete a fluid communication channel between the interior of blood treatment vial 38 and first tube 36. The blood treatment vial 38 can include an enhancement composition. Also, a first clip 40 can be coupled to the first tube 36 to regulate flow through first tube 36.

First tube 36 is coupled at its second end to an input of a Y-shaped connector 42. An in-line micro-biotic barrier filter 44 is positioned in the first tube 36 flow path to filter the material flowing from the vented spike 32 through the first tube 36 to the input of Y-shaped connector 42. One exemplary in-line micro-biotic barrier filter 44 is a flat 0.2 micron filter.

A transfer bag 46 can be coupled to a first end of a second tube 48. The second end of second tube 48 is coupled to the other input of Y-shaped connector 42. Transfer bag 46 can be initially empty and used to collect, for example, supernatant waste material. Additionally or alternatively, transfer bag 46 may initially include a processing agent, such as a wash solution. A second clip 50 can be coupled to the second tube 48 to regulate flow through second tube 48. Further, a second transfer bag 52 can be coupled to the second tube 48 by a third tube 54. The second transfer bag 52 can be initially empty and used to collect, for example, supernatant waste material. Additionally, or alternatively, transfer bag 52 may initially include a processing agent, such as an additive solution. A third clip 56 can be coupled to the second tube 48 to regulate flow through second tube 48.

Fourth tube 58 can be coupled to the output of the Y-shaped connector 42 at its first end. A second end of fourth tube 58 is defined by a seal 60 sealing the fluid channel of fourth tube 58. For example, seal 60 can be welded closed or to a fifth tube 62 coupled to a blood bag 64 using a radio frequency (RF) tube sealer (not shown). Additionally, the blood bag 64 can comprise a sixth tube 66 that can transfer treated blood to a subject. Given that no potential entry point of the Y-type tube set 30 is initially unsealed or unprotected by a micro-biotic barrier filter, this Y-type tube set 30 is functionally-closed. In other words, the Y-type tube set 30 provides a functionally-closed, sterile fluid pathway (via fourth tube 58) for blood enhancement composition from bottle 38 to be delivered into the blood bag 64.

Because the blood enhancement composition can be transferred to the volume of donated blood by a sterile, functionally-closed fluid pathway, the blood can be stored for more than 24 hours after such delivery. Additional post-processing devices can be used to further process the blood while maintaining the blood in a functionally-closed, sterile environment. For example, the volume of donated blood can be processed using a functionally-closed, sterile centrifuge. This can be done, for example, prior to delivering the enhancement composition to the volume of donated blood, contained in a blood bag, to remove components of whole blood and leave RBCs in the blood bag. One exemplary functionally-closed, sterile centrifuge is the COBE Spectra Apheresis System. Post-wash storage beyond 24 hours can be achieved using "functionally closed" blood cell processing systems such as the Haemonetics Blood Cell Processor model ACP 215.

Methods and systems among those of the present technology are illustrated in the following non-limiting examples.

EXAMPLE 1

A Y-type tube set is assembled is assembled as shown in FIG. 2 and connected to a unit of RBCs. The tube set includes a 0.2 μm filter. RBC enhancement composition (rejuvesol® Solution) is transferred to the RBCs via a vented spike to form a treated blood composition. The treated blood composition is mixed and incubated, forming an incubated blood composition. The treated blood composition is centrifuged to form a pellet of RBC and a supernatant. The supernatant is transferred to an empty waste bag, and the pellet of RBCs was resuspended in 100 mL additive solution that was transferred from a second transfer bag.

EXAMPLE 2

A Y-type tube set is assembled as shown in FIG. 2 and connected to a unit of 250 mL RBCs. 100 mL additive solution, comprising saline, was transferred to the RBCs. The tube set includes a 0.2 μm filter. 50 mL RBC enhancement composition (rejuvesol® Solution) was transferred to the RBCs via a vented spike to form a treated blood composition. The treated blood composition was mixed and incubated, forming an incubated blood composition. The incubated blood composition was then diluted with 200 mL wash solution from a first transfer bag containing 200 mL wash solution, forming a diluted blood composition. The diluted blood composition was centrifuged to form a pellet of RBCs and a supernatant. The supernatant was transferred to the now empty first transfer bag, and the pellet of RBCs was resuspended in 100 mL additive solution, which was transferred from a second transfer bag.

Figure 3:
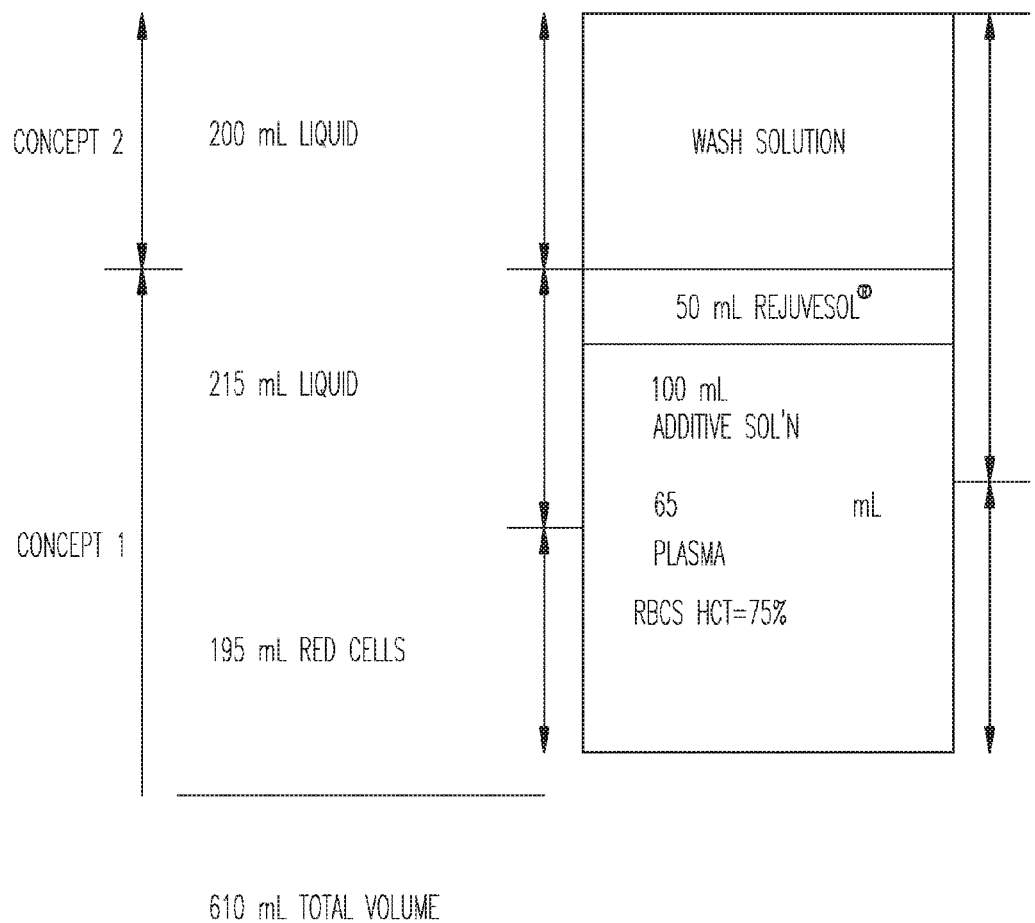
FIG. 3 is a diagrammatic illustration of two concepts of performing a method of the present technology.

The processing of blood as described in Examples 1 and 2 results in differing dilutions of Rejuvesol® constituents, as depicted in FIG. 3 and as described below.

Concept 1 Dilution of Rejuvesol®

$$\frac{215 \text{ mL}}{50 \text{ mL}} = 4.3$$

The concentration of each constituent of Rejuvesol® is $\geq 100$ mMol/L and would be $\geq 23.3$ mMol/L after centrifugation and removal of 75% of all supernatant where an estimated residual volume of 53.8 mL remains in the red cells.

Initial=23.3 mMol/L×0.215 mL=5.01 mMol

Final=23.3 mMol/L×0.0538L=1.23mMol

Est. % Residual of each constituent=25%

Concept 2 Dilution of Rejuvesol®

$$\frac{350 \text{ mL}}{50 \text{ mL}} = 7$$

The concentration of each constituent in Rejuvesol® is a $\geq 100$ mMol/L and would be $\geq 14.3$mMol/L after dilution, centrifugation, and removal of 75% of all supernatant where an estimated residual volume of 53.8 mL remains in the red cells.

Initial 143mMol/L×0.350 mL=5.01 mMol

Final=14.3 mMol/L×0.0538 L=0.0769 mMol

Est. % Residual of each constituent=15%

Blood processed according to Examples 1 and 2 are analyzed for concentrations of rejuvenation materials in the final processed RBC suspensions, with the following results.

TABLE 1

| | | Plasma Concentration in vivo* after transfusion of one unit of 2,3-DPG Enhanced Cells | | |
|---|---|---|---|---|
| Constituent or Metabolite | Reference Concentration in Serum or Plasma (mMol/L) | Without Further Processing (mMol/L)** | Concept 1, assumes 75% Removal (mMol/L) | Concept 2, assume 85% Removal (mMol/L) |
| Pyruvate | 0.034-0.102 | 2.19 | 0.55 | 0.33 |
| Adenine | n/a | 0.110 | 0.027 | 0.016 |
| Inosine | n/a | 2.19 | 0.55 | 0.33 |
| Phosphates | 0.74-1.52 | 2.19 | 0.55 | 0.33 |
| Lactate | 0.3-2.2 | 2.19 | 0.55 | 0.33 |
| Uric Acid | 0.16-0.51 | 2.19 | 0.55 | 0.33 |
| Hypoxanthine | 0.0001-0.0011 | 2.19 | 0.55 | 0.33 |

*Total Plasma Volume = 2.28 Liters
**Refer to 2000 Report by Dr. Lobe

The treatment of stored LR-RBCs with rejuvesol®, either concurrently or post storage prior to transfusion resulting in greater restoration of 2,3-DPG. Even though the pre-treatment packed cell weight of the LR-RBC units were greater than the NLR-RBC units (Table 1), recent studies demonstrate that the invention resulted in significantly higher concentration of 2,3-DPG to levels in LR-RBC derived from 500 mL of whole blood (WB) that were treated rejuvesol® solution when compared to NLR-RBC that were derived from 450 mL of WB (Table 2).

TABLE 2

| Pre-rejuvenation Net RBC Weight (grams) | | |
|---|---|---|
| LR-RBC Derived from | NLR-RBC Derived from 450 mL | |
| 350.1 | 338.1 | Mean (n = 14} |
| 18.3 | 19.5 | SD |
| 318.9-379.0 | 305.0-366.5 | Range |

TABLE 3

Summary; ATP and 2,3-DPG values after rejuvenation, deglycerolization, and 24-post deglycerolization

| LR-RBC Derived from 500 mL of WB | | NLR-RBC Derived from 450 mL of WB | | |
|---|---|---|---|---|
| ATP (μmol/gHbg) | 2,3-DPG (μmol/gHbg) | ATP (μmol/gHbg) | 2,3-DPG (μmol/gHbg) | |
| 7.94 | 11.04 | 7.55 | 8.13 | Mean Post-Rej (n = 14) |
| 1.09 | 1.54 | 0.73 | 1.60 | SD |
| 5.89-9.60 | 9.05-13.68 | 6.27-8.75 | 5.75-11.01 | Range |
| NS | † | NS | † | † $p < 0.0001$ |
|  |  |  |  | NS $p < 0.27$ |
| 7.50 | 16.72 | 7.82 | 13.91 | Mean Post Delyc (n = 13) |
| 0.48 | 1.64 | 0.68 | 1.89 | SD |
| 6.62-8.94 | 13.67-19.58 | 6.80-9.20 | 11.17-17.29 | Range |
| NS | * | NS | * | * $P < 0.0005$ (n = 13) |
|  |  |  |  | NS $p < 0.77$ |
| 7.59 | 17.73 | 8.39 | 15.64 | Mean 24-hr Post Deglyc (n = 14) |
| 0.85 | 2.08 | 0.91 | 1.48 | SD |
| 6.62-9.05 | 13.42-20.87 | 6.76-9.53 | 12.73-18.59 | Range |
| NS | + | NS | + | + $p < 0.0058$ |
|  |  |  |  | NS $p < 0.77$ |

The embodiments and the examples described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "preferred" or "preferable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

What is claimed is:

1. A method for transfusing blood to a mammalian subject, the method comprising, the steps of:
    fluidly connecting a container of red blood cells to an output of a Y-type connector of a sterile, closed processing system;
    fluidly connecting a container comprising an enhancement composition to a first input of the Y-type connector of the closed processing system, the enhancement composition comprising inosine, adenine, pyruvate, sodium phosphate, or a combination thereof;
    flowing the enhancement composition through a filter of the closed processing system and into the container of red blood cells to form a treated red blood cell composition; and
    incubating the treated red blood cell composition, forming an incubated red blood cell composition comprising treated red blood cells;
    fluidly connecting a transfer bag to a second input of the Y-type connector, the transfer bag comprising a wash solution;
    washing the treated red blood cells, including flowing the wash solution through the Y-type connector and into the treated red blood cells; and
    administering the treated red blood cells to the subject after the washing step.

2. The method of claim 1, wherein the enhancement composition comprises:
    from about 25 g/L to about 30 g/L of inosine;
    from about 0.2 g/L to about 2 g/L of adenine;
    from about 5 g/L to about 15 g/L of pyruvate;
    from about 17 g/L to about 23 g/L of sodium phosphate;
    or a combination thereof.

3. The method of claim 1, wherein the enhancement composition comprises about 27 g/L inosine, about 11 g/L pyruvate, about 0.7 g/L adenine, and about 21 g/L phosphate mixture, and has a pH from about 6.5 to about 7.5.

4. The method of claim 1, wherein the container of red blood cells was stored at a preservation temperature prior to the fluidly connecting step.

5. The method of claim 1, further comprising separating the treated red blood cells from the enhancement composition before the administering step.

6. The method of claim 5, wherein separating the treated red blood cells from the enhancement composition includes flowing the enhancement composition through the Y-type connector and into the transfer bag.

7. The method of claim 1, further comprising separating the wash solution from the treated red blood cells prior to the administering step.

8. The method of claim 1, wherein the incubating is from about 30 minutes to about 90 minutes at a temperature of from about 35° C. to about 40° C.

9. The method of claim 1, further comprising processing the incubated red blood cell composition to form a pellet of treated red blood cells.

10. The method of claim 9, wherein the transfer bag further includes an additive solution, separated from the wash solution, the method further comprising flowing the additive solution through the Y-type connector and into the container to suspend the pellet of treated red blood cells in the additive solution.

11. A method for improving the metabolic function of blood, comprising:
    fluidly connecting a container comprising a volume of red blood cells to a sterile, closed processing system comprising a first tube configured for fluid communication with the container, a first transfer bag and a second transfer bag contemporaneously coupled to a second tube of the closed processing system;
    fluidly connecting an enhancement composition to the closed processing system, including adding the enhancement composition to the volume of red blood cells to form a treated blood composition;
    incubating the treated blood composition to form an incubated red blood cell composition; and
    processing the incubated red blood cell composition to separate the red blood cells and a fluid comprising the enhancement composition, the red blood cells having an enhanced metabolic function.

12. The method of claim 11, wherein the first transfer bag comprises a wash solution, the method further comprising diluting the incubated red blood cell composition with the wash solution prior to the processing step.

13. The method of claim 11, wherein processing includes collecting the fluid in the first transfer bag or the second transfer bag.

14. The method of claim 11, wherein the second transfer bag has an additive solution, and wherein processing includes collecting the fluid in the first transfer bag and flowing the additive solution into the separated red blood cells after collecting the fluid in the first transfer bag.

15. The method of claim 11, wherein the enhancement composition comprises:
    from about 25 g/L to about 30 g/L of inosine;
    from about 0.2 g/L to about 2 g/L of adenine;

from about 5 g/L to about 15 g/L of pyruvate;
from about 17 g/L to about 23 g/L of sodium phosphate; or
a combination thereof.

16. The method of claim 11, wherein the enhancement composition comprises:
from about 25 g/L to about 30 g/L of inosine;
from about 0.2 g/L to about 2 g/L of adenine;
from about 5 g/L to about 15 g/L of pyruvate; and
from about 17 g/L to about 23 g/L of sodium phosphate.

17. The method of claim 11, wherein the enhanced metabolic function increases the concentration of 2,3-diphosphoglycerate, adenosine triphosphate, or both, in the red blood cells.

18. The method of claim 11, further comprising administering to a subject the red blood cells having an enhanced metabolic function.

19. The method of claim 18, wherein the subject is experiencing sepsis, septic shock, Upper Gastrointestinal Bleeding (UGIB), anemia, severe trauma, heart attack or stroke.

* * * * *